United States Patent [19]

Lundrigan et al.

[11] Patent Number: 5,205,814

[45] Date of Patent: Apr. 27, 1993

[54] LUMBAR SUPPORT DEVICE

[76] Inventors: John C. Lundrigan, 11451 Goose Lk. Rd., Champlin, Minn. 55316; Fabio Lopez, 27913-145th St., Zimmerman, Minn. 55398

[21] Appl. No.: 890,856

[22] Filed: Jun. 1, 1992

[51] Int. Cl.$^5$ ............................................. A61F 5/00
[52] U.S. Cl. ................................ 602/19; 128/DIG. 20
[58] Field of Search .................. 602/13, 19, 12, 5; 128/DIG. 20, 876; 297/284

[56] References Cited

U.S. PATENT DOCUMENTS

| | | | |
|---|---|---|---|
| 4,135,503 | 1/1979 | Romano | 602/19 |
| 4,552,135 | 11/1985 | Racz | 602/19 |
| 4,597,386 | 7/1986 | Goldstein | 602/19 |
| 4,669,455 | 6/1987 | Bellati | 602/13 |
| 4,682,587 | 7/1987 | Curlee | 602/13 |
| 4,682,588 | 7/1987 | Curlee | 602/13 |
| 4,709,692 | 12/1987 | Kirschenberg | 602/19 |
| 4,756,306 | 7/1988 | Curlee | 602/19 |
| 4,768,499 | 9/1988 | Kemp | 602/19 |
| 5,062,414 | 11/1991 | Grim | 602/19 |
| 5,085,214 | 2/1992 | Barrett | 128/DIG. 20 |

*Primary Examiner*—Robert A. Hafer
*Assistant Examiner*—Michael Brown
*Attorney, Agent, or Firm*—Leo Gregory

[57] ABSTRACT

A lumbar region yielding support device adapted to be adjustably body positioned to be body worn or adjustably positioned attached to a seating structure.

10 Claims, 3 Drawing Sheets

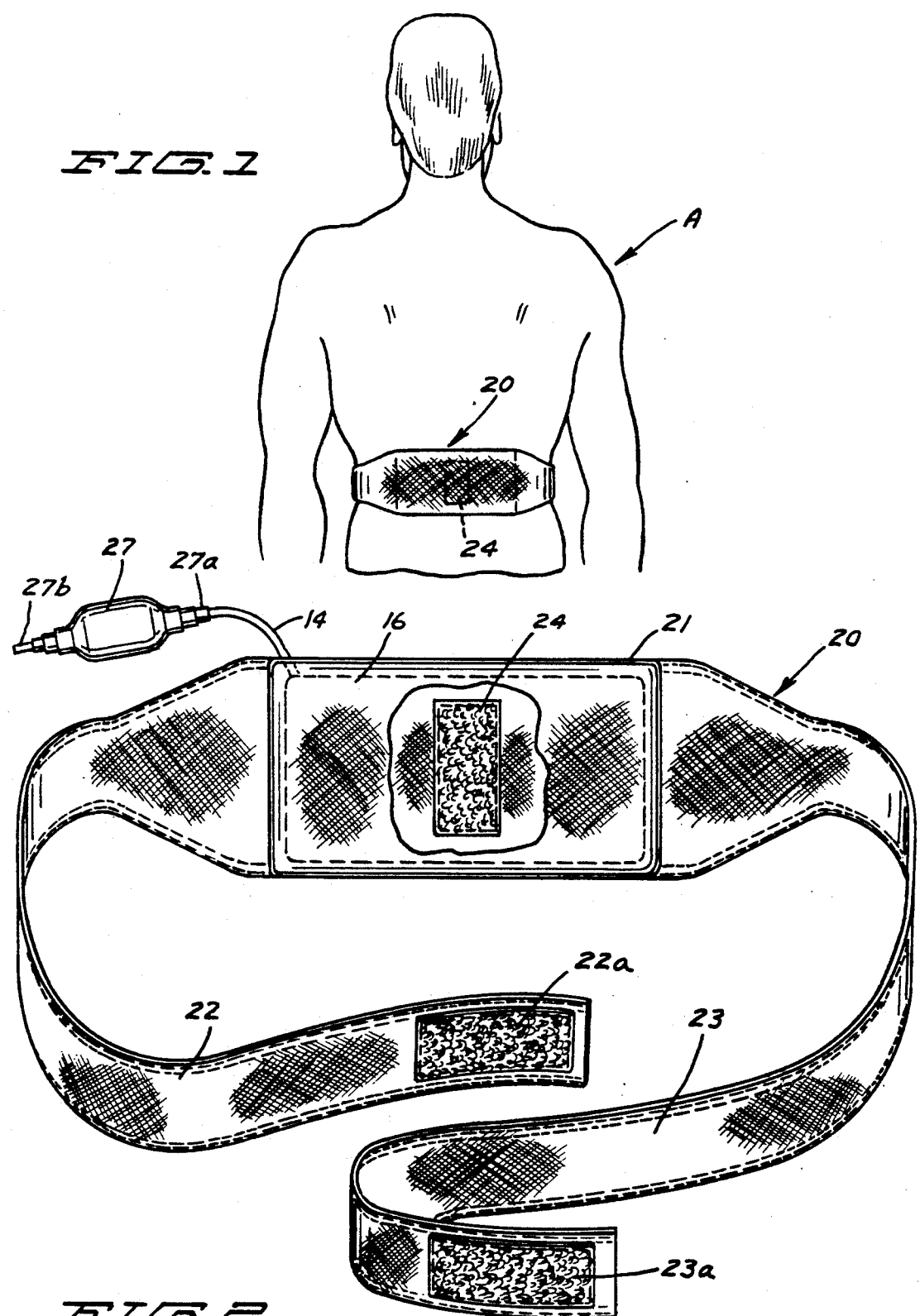

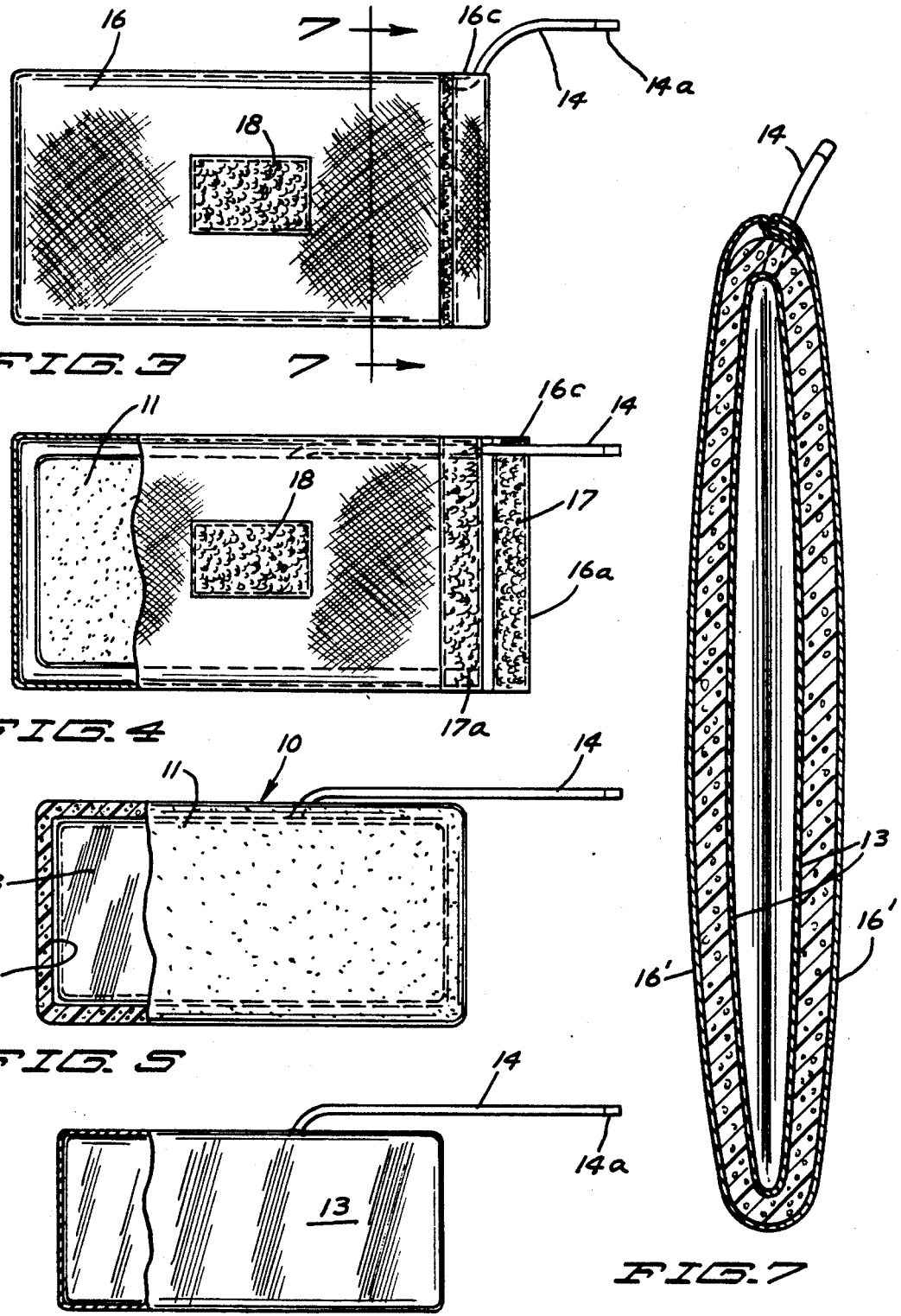

LUMBAR SUPPORT DEVICE

BACKGROUND OF THE INVENTION

1. Field of Invention

This invention relates to a variably positioned lumbar support member.

2. Brief Description of the Previous Art

The device comprising the invention herein is a medically-oriented device in a very active art.

Back support members to alleviate aches and pains are very prevalent.

A good many support devices are embodied into seating arrangements including vehicle seats as indicated in the following patents.

In U.S. Pat. No. 3,974,827 to Bodeen a bladder is embodied within a device to project a portion thereof for relief pressure. In U.S. Pat. No. 4,431,232 to Hamnouche a curved cushion is provided to overlie a seat back for pressure application to a back. In U.S. Pat. No. 4,471,993 to Watson a semi-rigid support is provided with strap fasteners to secure the same to a seat back. In U.S. Pat. No. 4,597,386 to Goldstein a panel cushion combination is presented with attaching straps to secure the same to a seat back. In U.S. Pat. No. 4,789,202 to alter a vehicle cushion is shown embodying an inflatable element for application of back pressure.

SUMMARY OF THE INVENTION

It is desirable to have an appropriately inflatable cushion which may be conveniently adapted to be applied to a seat back or to be worn upon the body as a garment for application of a constant pressure to relieve back stress and when worn not to give an unsightly garment appearance.

These and other objects and advantages of the invention will be set forth in the following description made in connection with the accompanying drawings in which the reference characters refer to similar parts throughout the several views.

BRIEF DESCRIPTION OF THE DRAWINGS

FIG. 1 is a view in rear elevation of a cushion holding band in operating position;

FIG. 2 is a view of the cushion holding band of FIG. 1 partially in front elevation holding in elevation the cushion of the invention herein and the remainder of said band is in perspective;

FIG. 3 is a view in elevation of the envelope containing the cushion of the invention herein;

FIG. 4 is a view in elevation similar to that of FIG. 3 with a portion broken away showing a cushion therein and the closure flap thereof being in open position;

FIG. 5 is a view in front elevation of the cushion herein with a portion broken away showing a bladder therein;

FIG. 6 is a plan view of the bladder herein with a portion thereof broken away;

FIG. 7 is a view in section taken on line 7—7 of FIG. 3 as indicated;

DESCRIPTION OF A PREFERRED EMBODIMENT

Figure 8:
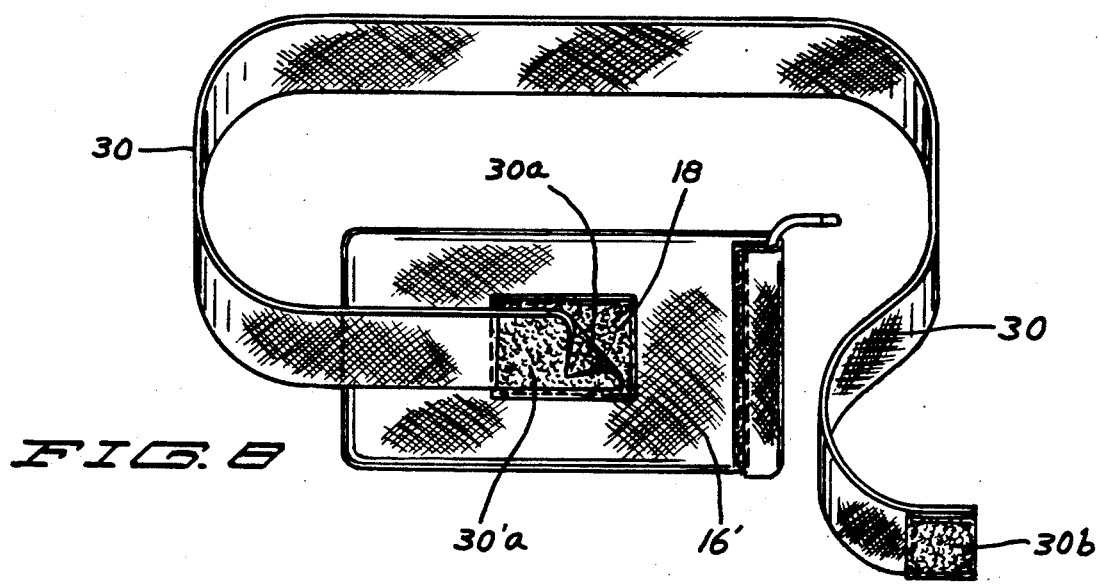
FIG. 8 is an alternate band or strap shown partially in elevation holding the cushion herein and the remainder thereof being in perspective.

Back pain is widely suffered by most everyone resulting from faulty posture, uncomfortable seating and from prolonged periods of sitting as traveling in a vehicle. Cushions and back support members of various other kinds are prevalent as accessories such as being attached to or merely applied to or positioned on a seat.

As will be described herein, it is desirable to have an appropriate support to be attached to or positioned on a seat but it is very desirable in many particularly chronic cases to apply a stress relieving means directly to the body to be worn as if it were a piece of attire and yet give no outward appearance that anything more than merely ordinary attire is being worn.

Referring to the Figs. and particularly to FIG. 5, a cushion 10 is shown partially in section. The outer shell 11 of said cushion is of a compressible flexible material such as a foam plastic sheet material and the same has therein for substantially the full extent thereof a cavity 12. Disposed within said cavity is an inflatable bladder 13 having an air tube 14 extending therefrom. Said air tube has a terminal self closing valve 14a. Said valve yields to pressure such as the pressure of incoming air for inflation or to the pressure of suction for withdrawal of air or deflation.

Referring to FIGS. 3 and 4, an outer container or envelope 16 is shown within which said cushion 10 is contained for use and as contained within said envelope said cushion 10 is referred to as a cushion device 16'. Said envelope is suitably made of an appropriate nylon sheet material which is durable, flexible and readily kept clean. Said envelope has an end closure flap 16a which is lined with a self sealing strip of Velcro 17 which in closure overlies a companion self securing Velcro strip 17a. Velcro fasteners are in common use and no particular description of a Velcro strip is believed to be necessary. As indicated in FIG. 3, said air tube extends outwardly of an unsealed end portion 16c of said flap 16a.

Securing centrally of one side of said envelope is a self securing Velcro strip 18.

Said envelope 16 is of a size to nicely overlie a stressed portion of the lumbar region of the back of a user.

The cushion exerts a pressure by being inflated however a force must be exerted upon the cushion to cause the pressure of inflation of the cushion to be applied to a stressed area of a back to provide relief.

Referring to FIGS. 1 and 2, a band 20 is shown as applied to a body A. This band preferably is made of a non-metallic non-stretchable material which very closely encompasses the body as if it were an article of attire. The central portion 21 of said band is of a size to nicely overlie said cushion device 16'. Said band has a Velcro strip 24 which is self securing in overlying or engaging said Velcro strip 18.

Extending from said central portion of said band 20 are end strips 22 and 23 and at their outer end portions are Velcro strips 22a and 23a which releasably secure said end portions together.

With respect to the air tube 14, a squeeze type of air pump 27 is shown which pumps air into said bladder with its inlet valve 27a and withdraws air therefrom to deflate the same with its suction valve 27b.

When said cushion device is positioned and worn as shown in FIG. 1 about a body A, the band 20 being non-stretchable, when fastened snugly about the body confines the cushion device very closely to the body to prevent outward bulging and to cause the pressure of the inflated cushion to bear very effectively against the body. Hence only a minimum amount of inflation is required to receive wholly adequate relief from the use of said cushion device.

Although said band has been described as being particularly adaptable for body use, when desired, said band may be reversed and disposed about a seat back with the cushion device facing outwardly. Here relief is secured by a user being in a sitting position and pressing his back against the inflated cushion device. See FIG. 9.

To refer back to a direct application to the body, when worn under outer garments as if an article of attire, stress is voided where it would otherwise very likely develop, particularly in long duration sitting positions such as during a long motor drive where there is very little shifting in position, if any. The application of this cushion device is an important factor in having the user assume correct posture in sitting and to maintain correct posture for the whole duration of sitting. Correct posture avoids back stress.

Figure 9:
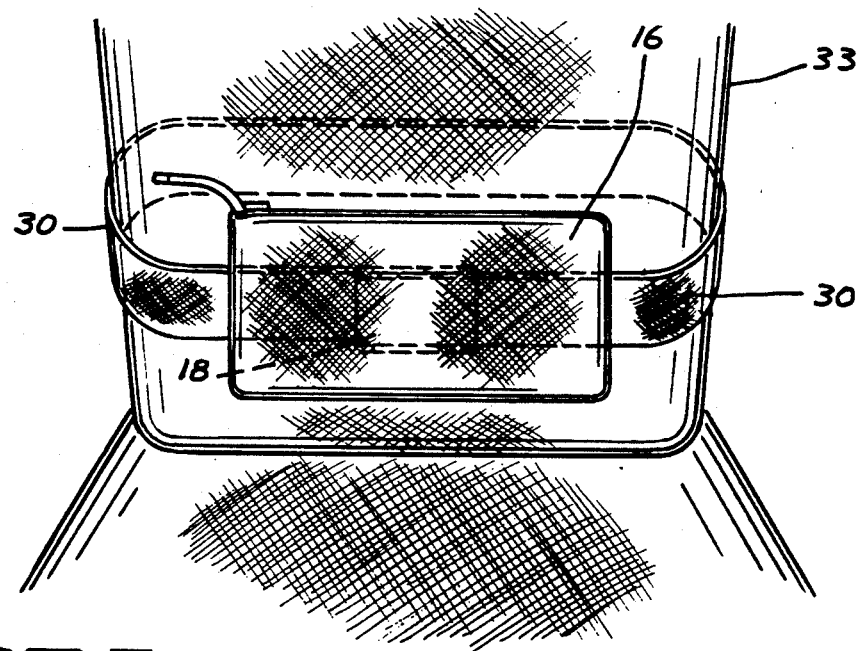
FIG. 9 is a view similar to that of FIG. 8 partially in front plan and partially in perspective.

Referring to the FIGS. 8 and 9, a strap or band 30 is shown in connection with the cushion device 16'. Said strap 30 is wholly elastic and stretchable under a considerable pull effort or tension. Said strap has self securing Velcro strip terminal portions 30'a and 30b. The strip 30b overlies only a portion of the length of the strip 30'a being only about one third as long. On the opposite side of the strip 30'a is a corresponding Velcro strip 30a. This arrangement will be explained.

As shown in FIG. 8, the strap 30 may be disposed about a body in the manner of the band 20 as in FIG. 1. The terminal strips 30'a and 30b will interlock. As a practical matter, the strap will be secured in the front of the body, the cushion device 16' will be inserted thereunder and fastened by its Velcro strip interlocking with the exposed portion of the strip 30a. Then the band and cushion device are slid around the body to engage the lumbar region. This would be the procedure where a person applies the strap and support cushion device to himself.

Referring to FIG. 9, here the strap is disposed about a back support 33 and the terminal strips 30'a and 30b interengage to secure the belt. Here the Velcro strip 30a is facing outwardly and the cushion device 16' by its Velcro strip 18 is secured to the exposed Velcro strip 30a.

Thus it is seen that I have provided a very practical application of a pressurized cushion for the relief of lumbar stress, which device in what is regarded as its most generally used application is worn as if an article of attire giving no discernible evidence of a body support device being worn.

Figure 10:
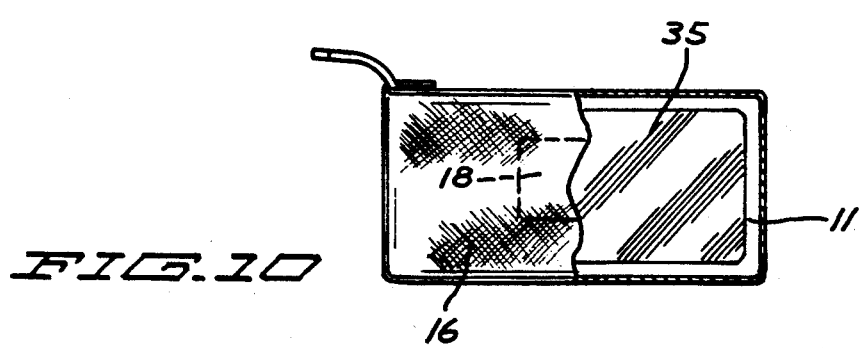
FIG. 10 is a plan view showing a modification.

An additional feature is present as indicated in FIG. 10. Here a conventional thermal pad 35 is inserted into the envelope 16 overlying the cushion 11. Thus here additional therapy is applied in the nature of a hot or cold pack, whichever is appropriate for the particular condition at hand.

It will of course be understood that various changes may be made in the form, details, arrangement and proportions of the device herein without departing from the scope of the invention which generally stated, consists in a device capable of carrying out the objects and purposes above set forth, in the parts and combination of parts disclosed and defined in the appended claims.

What is claimed is:

1. A flexible lumbar support, comprising
   a lumbar support cushion device to be positioned to engage a specific back portion area as desired,
   a compressible foam forming a cushion disposed into said cushion device,
   said cushion having a cavity therein substantially the full extent thereof,
   an inflatable bladder disposed within said cavity,
   inflating means in connection with said bladder,
   a body encompassing band,
   releasable securing means attached to said band centrally thereof,
   means for releasable attachment to said securing means carried by said cushion device,
   said cushion device by said last mentioned means being secured to said band, whereby
   said band is disposed about a body carrying said cushion device, in pressurized engagement with said specific back area without disturbing the outer appearance of the attire worn about the body.

2. The structure of claim 1, wherein said band is formed of a non-stretchable material.

3. The structure of claim 1, wherein
   said band comprises an elastic strap having end portions adapted to be releasably secured to each other.

4. The structure of claim 1, including
   a thermal unit overlying said cushion within said cushion device.

5. A flexible lumbar support, comprising
   an envelope,
   a support cushion to overlie the lumbar area of a back disposed within said envelope,
   a compressible foam forming said cushion,
   a cavity within said cushion substantially the full extent thereof,
   an inflatable bladder within said cavity,
   a band,
   releasable securing means attached to said band, and
   releasable securing means carried by said envelope for attachment thereof to said band.

6. The structure of claim 5, wherein
   said band is adapted to overlie the lumbar area of a body.

7. The structure of claim 5, wherein
   said band is adapted to encircle a seat back to position said cushion device for support of the lumbar region of a body bearing thereagainst.

8. The structure of claim 6, including
   a releasable self sealing flap of said envelope.

9. A lumbar support device, comprising
   a flexible cushion to overlie the lumbar region of a body, said cushion having an outer surface yielding layer,
   a cavity formed within said cushion substantially the full extent thereof,
   an inflatable bladder disposed within said cavity and having an air tube extending outwardly of said cushion,
   an envelope of appropriate material containing said cushion, the same having an outlet for said air tube.

10. The structure of claim 9, including
    a thermal pad overlying said cushion within said envelope.

* * * * *